United States Patent
Kummer et al.

(10) Patent No.: US 7,077,126 B2
(45) Date of Patent: Jul. 18, 2006

(54) INHALATION THERAPY MASK AND DEVICE FOR ANIMALS

(75) Inventors: Frank Kummer, Munich (DE); Martin Luber, Munich (DE); Markus Mornhinweg, Diessen (DE)

(73) Assignee: Pari GmbH Spezialisten fur effektive Inhalation, Stamberg (DE)

( * ) Notice: Subject to any disclaimer, the term of this patent is extended or adjusted under 35 U.S.C. 154(b) by 0 days.

(21) Appl. No.: 10/850,047

(22) Filed: May 19, 2004

(65) Prior Publication Data

US 2004/0250816 A1 Dec. 16, 2004

(30) Foreign Application Priority Data

May 19, 2003 (DE) ................................ 103 22 505

(51) Int. Cl.
*A61M 11/00* (2006.01)
*A62B 18/02* (2006.01)

(52) U.S. Cl. ........................... 128/200.23; 128/206.21; 128/207.13

(58) Field of Classification Search ........... 128/200.14, 128/200.23, 200.22, 200.19, 200.12, 200.21, 128/206.21, 207.13, 206.27
See application file for complete search history.

(56) References Cited

U.S. PATENT DOCUMENTS

| | | | | |
|---|---|---|---|---|
| 2,312,714 A | * | 3/1943 | Herbin | 128/206.15 |
| 3,491,755 A | | 1/1970 | Barghini et al. | |
| 4,546,768 A | * | 10/1985 | Ferierabend | 128/200.16 |
| 4,953,546 A | * | 9/1990 | Blackmer et al. | 128/203.16 |
| 4,955,372 A | * | 9/1990 | Blackmer et al. | 128/203.16 |
| 5,062,423 A | * | 11/1991 | Matson et al. | 128/207.15 |
| 5,249,570 A | * | 10/1993 | Cox | 128/206.28 |
| 5,666,948 A | * | 9/1997 | Matson | 128/200.23 |
| 5,954,049 A | | 9/1999 | Foley et al. | |

FOREIGN PATENT DOCUMENTS

| | | |
|---|---|---|
| DE | 693 12 473 T2 | 2/1998 |
| DE | 299 22 521 U1 | 4/2000 |
| DE | 101 25 564 | 11/2002 |
| EP | 0 537 991 A2 | 4/1993 |
| EP | 0 623 011 B1 | 7/1997 |
| EP | 1 229 855 B1 | 4/2003 |

* cited by examiner

*Primary Examiner*—Henry Bennett
*Assistant Examiner*—Annette Dixon
(74) *Attorney, Agent, or Firm*—Merchant & Gould P.C.

(57) ABSTRACT

To increase the accuracy of the administration of doses of inhalation therapies for animals, the invention proposes a two-part inhalation mask for animals in which each mask part (9) comprises an aerosol chamber (1) and an adaptation chamber (2). The two chambers are separated by a dividing wall (3) with an opening for the aerosol so that during the inhalation phases, the aerosol passes together with the respiratory air out of the aerosol chamber (1) into the adaptation chamber (2).

16 Claims, 5 Drawing Sheets

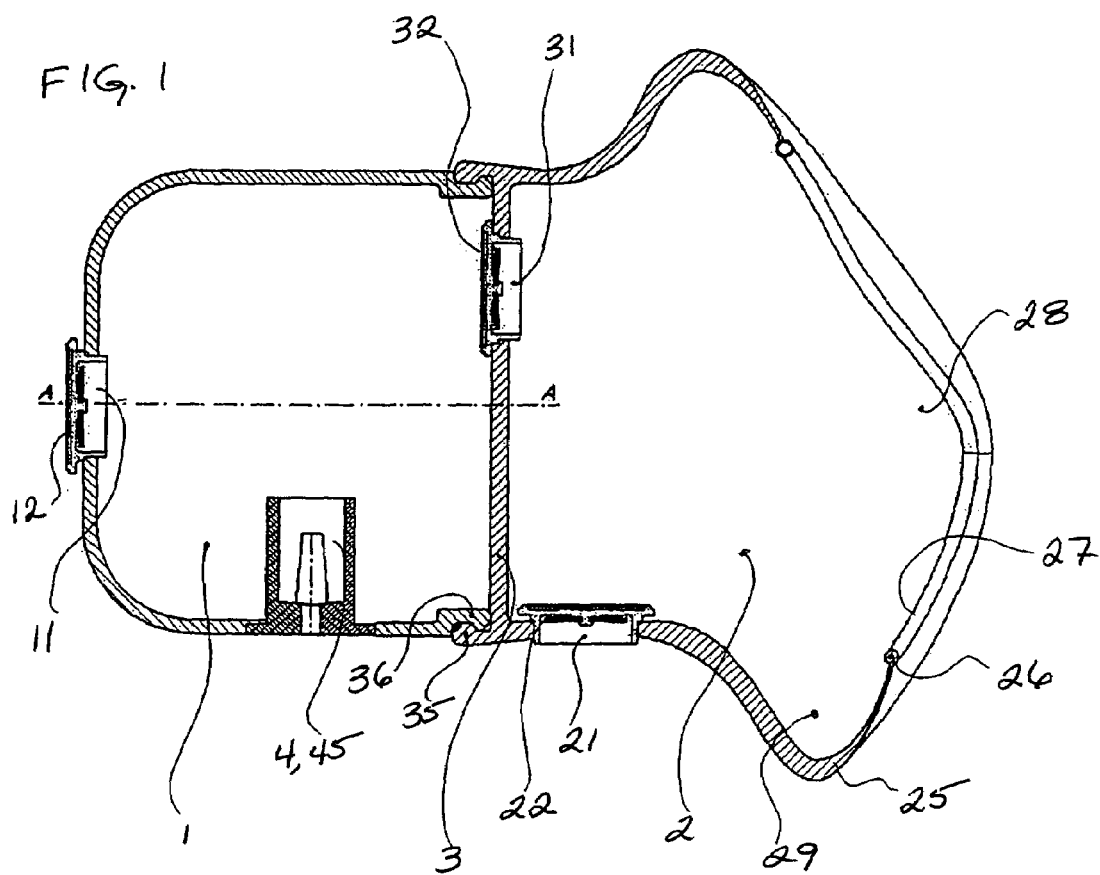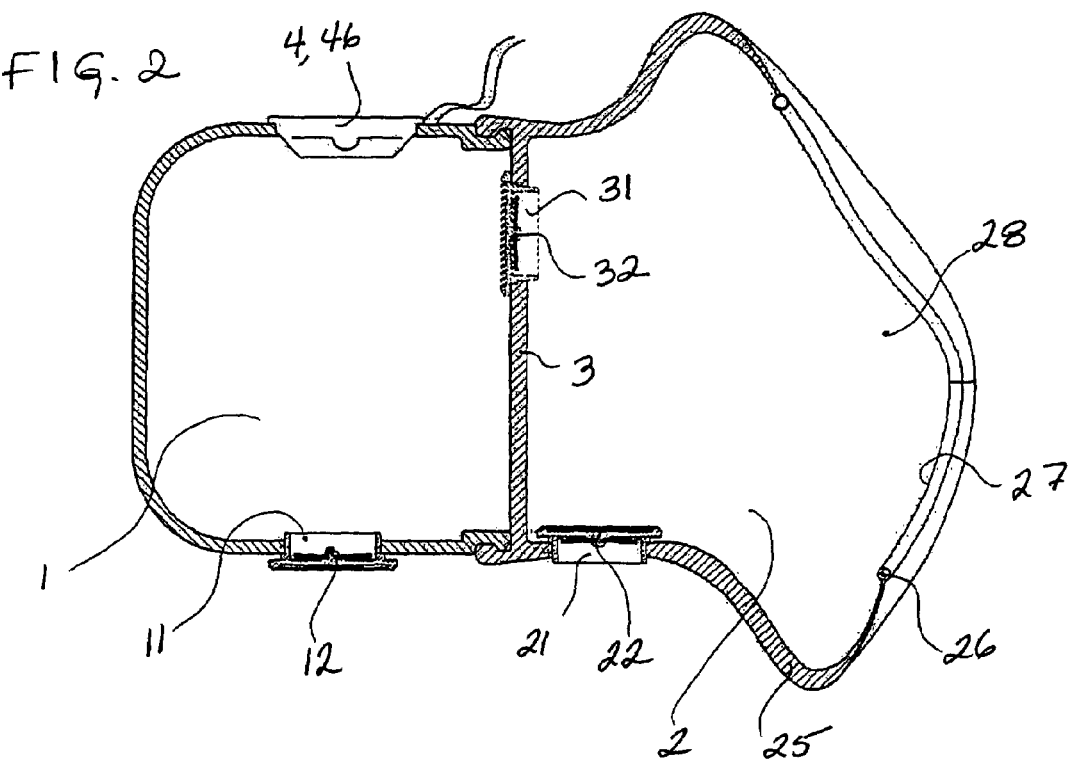

INHALATION THERAPY MASK AND DEVICE FOR ANIMALS

DESCRIPTION

Figure 3:
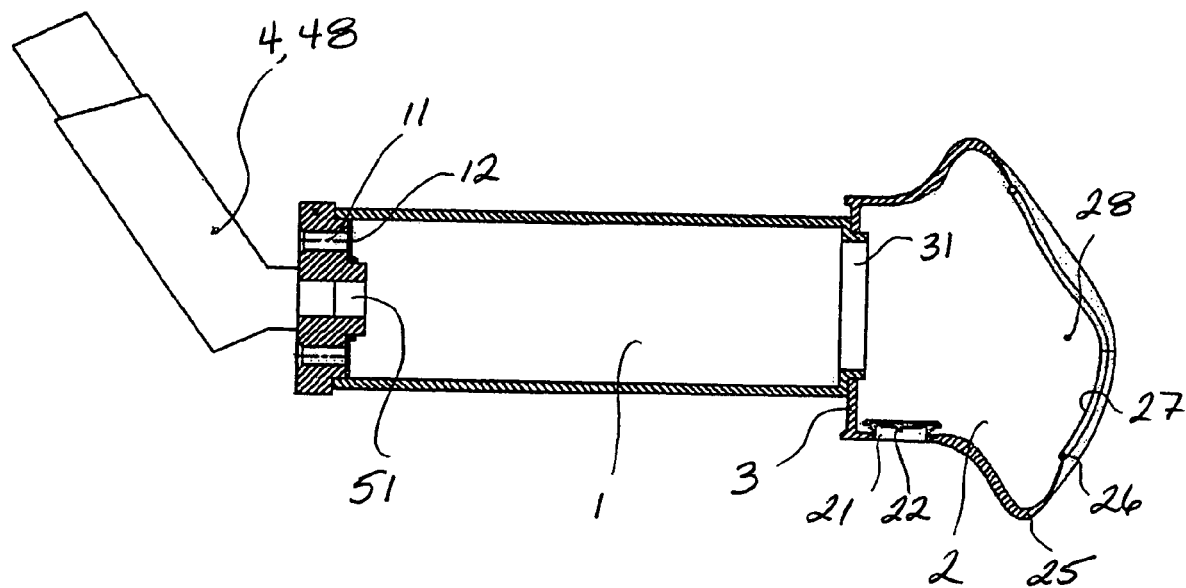

The invention relates to an inhalation therapy device for animals permitting the administration of precise doses of medication to animals.

Various therapy masks for horses are known from U.S. Pat. No. 5,954,049. The masks are placed on the front portion of a horse's head and secured so that the interior of the mask encloses the two respiratory openings in the nose (nostrils). The masks have inhalation and exhalation openings that are provided with valves for controlling the respiratory air flows established. Even though the shapes of the different masks and the location of the respiratory openings and valves are different, common to all the therapy masks is the fact that an aerosol generated by a single aerosol is supplied through the entire interior of the mask to the respiratory openings. However, this means the aerosol passes over large areas of the body surface of the front portion of the horse's head where it may settle without reaching the respiratory openings.

A therapy mask with a similar structure is known from EP 0 623 011 in which the aerosol is supplied from two or more aerosol generators through the interior of the mask to the animal's respiratory openings. Once again, with this known mask, the aerosol may settle on the animal's body surface and hence lose its therapeutic function.

Since the amount of aerosol lost cannot be determined, the known solutions are unfavourable because they do not permit the precise dose administration desirable for animals as well when using aerosol therapy.

The object to be achieved by the invention therefore consists in identifying an inhalation therapy mask that may used to achieve a more precise administration of doses for animals as well.

The solution according to the invention consists in an inhalation therapy mask for animals with two mask parts with one mask part being intended for arrangement over one of the animal's respiratory openings and each mask part comprising:

an aerosol chamber for receiving an aerosol generated by an aerosol generator with one inhalation opening with an inhalation valve through which respiratory air enters the aerosol chamber during the inhalation phases, an adaptation chamber surrounding one respiratory opening designed to adapt the mask part to the animal's external body surface with an opening directed toward the animal's respiratory opening with a circumferential inwardly curved sealing lip on its edge and with an exhalation opening with an exhalation valve through which respiratory air escapes from the adaptation chamber during the exhalation phases, and a dividing wall between the two chambers with a through-opening through which an aerosol present in the aerosol chamber passes together with the respiratory air from the aerosol chamber into the adaptation chamber during the inhalation phases.

The division of the mask into two parts means that each mask part may be designed for arrangement on one of the animal's respiratory openings so that the size and shape of each mask part may be matched precisely to the respiratory opening. Each mask part has an aerosol chamber and an adaptation chamber. An aerosol generated by an aerosol generator enters the aerosol chamber, which has an inhalation opening with an inhalation valve, and is stored there during the exhalation phases and supplied to the animal together with the respiratory air during the inhalation phases. The two chambers are separated from each other by a dividing wall so that there are no undesirable influences on the aerosol in the aerosol chamber during the exhalation phases. To ensure that the aerosol is supplied to the animal during the inhalation phases, the dividing wall has a through-opening through which an aerosol present in the aerosol chamber passes together with the respiratory air from the aerosol chamber into the adaptation chamber during the inhalation phases. The adaptation chamber is primarily intended for adapting the mask part to the body surface at the animal's respiratory opening. The correspondingly shaped opening in the mask part that is placed on the animal's respiratory opening has an inwardly folded sealing lip that in particular with a free end ensures the necessary highly flexible sealing of the mask interior. In addition, the adaptation chamber also has an exhalation opening with an exhalation valve.

In one advantageous embodiment, a separating valve designed to be open during the inhalation phases and closed during the exhalation phases is provided at the through-opening in the dividing wall. This valve provides enhanced protection for the aerosol chamber during exhalation phases.

For the alignment of the chambers in relation to each other, it is advantageous for the aerosol chamber to be attached in a positionable manner to the adaptation chamber.

To facilitate the separation of the chambers from each other for purposes of cleaning, advantageously provided on the aerosol chamber is a first latching device that interacts with a second latching device provided on the adaptation chamber to fix the aerosol chamber to the adaptation chamber.

In a favourable embodiment from the point of view of production, the first latching device is implemented as a latching projection and the second latching device is implemented as a latching groove. Due to the essentially rotationally symmetrical design of the aerosol chamber and an correspondingly adapted adaptation chamber, the latching projection and the latching groove can run round the circumference of the chamber in question so that the two chambers may be twisted in relation to each other when the latching projection slides along the latching groove. In addition, the latching projection and latching groove offer the advantage that it is easy to separate and reassemble the two chambers.

In one advantageous embodiment, the sealing lip is embodied as a continuation of the wall of the adaptation chamber thus enabling the adaptation chamber to be produced as a single-piece component. To provide a reliable seal, the thickness of the sealing lip diminishes in the direction of the adaptation chamber. The seal may be optimised by providing a bead on the edge of the sealing lip facing the adaptation chamber opening. The bead also protects the sealing lip with its diminishing thickness against damage in particular if the bead comprises solid material.

For cases when only one mask part is to be used, the mask parts may be separated from each other.

For attachment to the head of the animal, in one special embodiment, the mask parts are connected to a holding device for positioning the mask parts in relation to the respiratory opening. The holding device may take the form of holding straps or a holding band or a holding stocking, whereby the last item may be pulled over the head or part of the animal's head.

The mask according to the invention may be used with various aerosol generators as long as the aerosol generated by the aerosol generator is released into the aerosol chamber. In one advantageous embodiment, the aerosol generator is arranged in the aerosol chamber. However, the aerosol generator may also be arranged in a nebuliser chamber connected to the aerosol chamber for supplying the aerosol generated thus enabling conventional inhalation nebulisers to be used with the mask according to the invention. The aerosol generator may be a jet nebuliser, diaphragm nebuliser, ultrasonic nebuliser or spray nebuliser.

To create a complete system, the inhalation therapy device may be provided with at least one pocket for supply components that is designed to be arranged and secured on the animal's back. The pocket may be used to accommodate compressors and/or power supplies and/or electrical control elements that are then arranged on the animal's back. This arrangement has been found to be particularly suitable when used with horses since this enables the mask parts to be restricted to the necessary, but generally light, components and the supply components, which often frequently emit loud noises, to be positioned on the back. In view of the fact that the mask is divided into two parts, it is advantageous to provide two pockets, each assigned to one mask part, in order to accommodate the supply components for the mask part to which they are assigned. In addition to the supply components, it is also possible to accommodate the aerosol generator(s) in the pocket(s).

The invention will now be described with reference to the examples of the embodiments shown in the diagrams.

Figure 4:
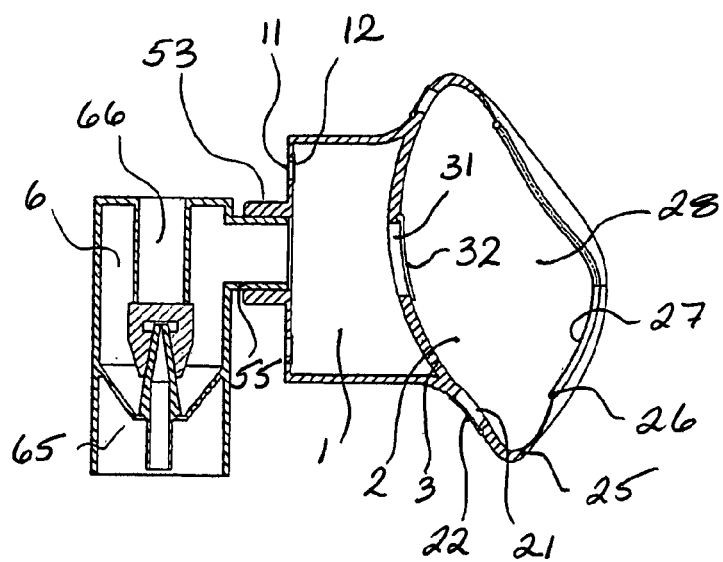
Figure 5:
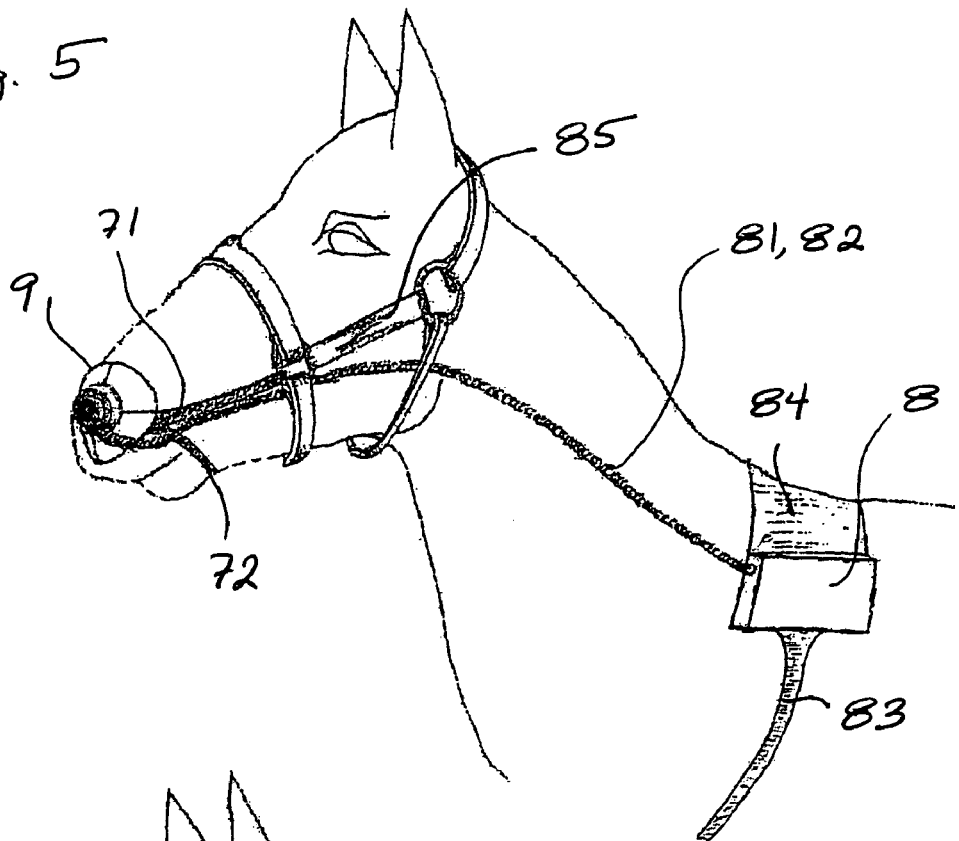
Figure 6:
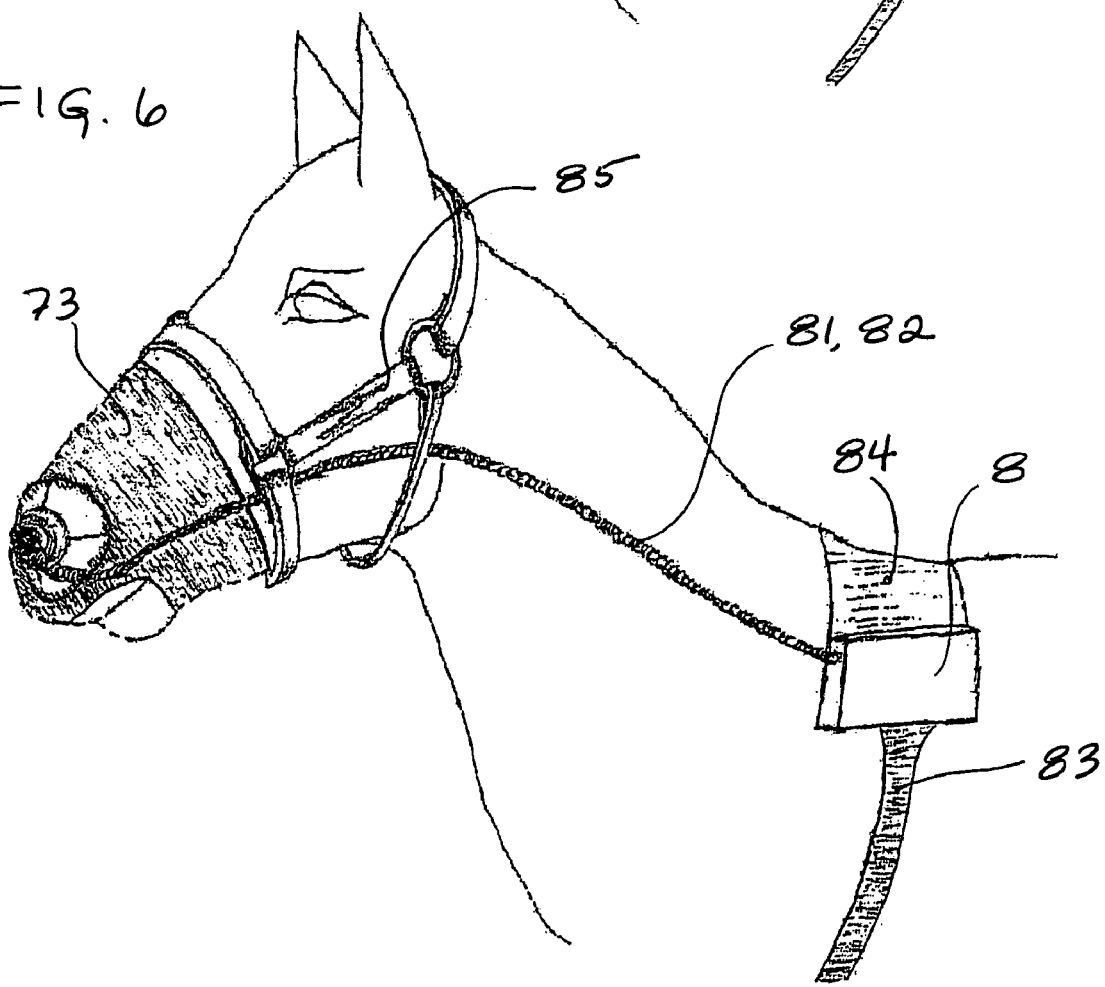
Figure 7:
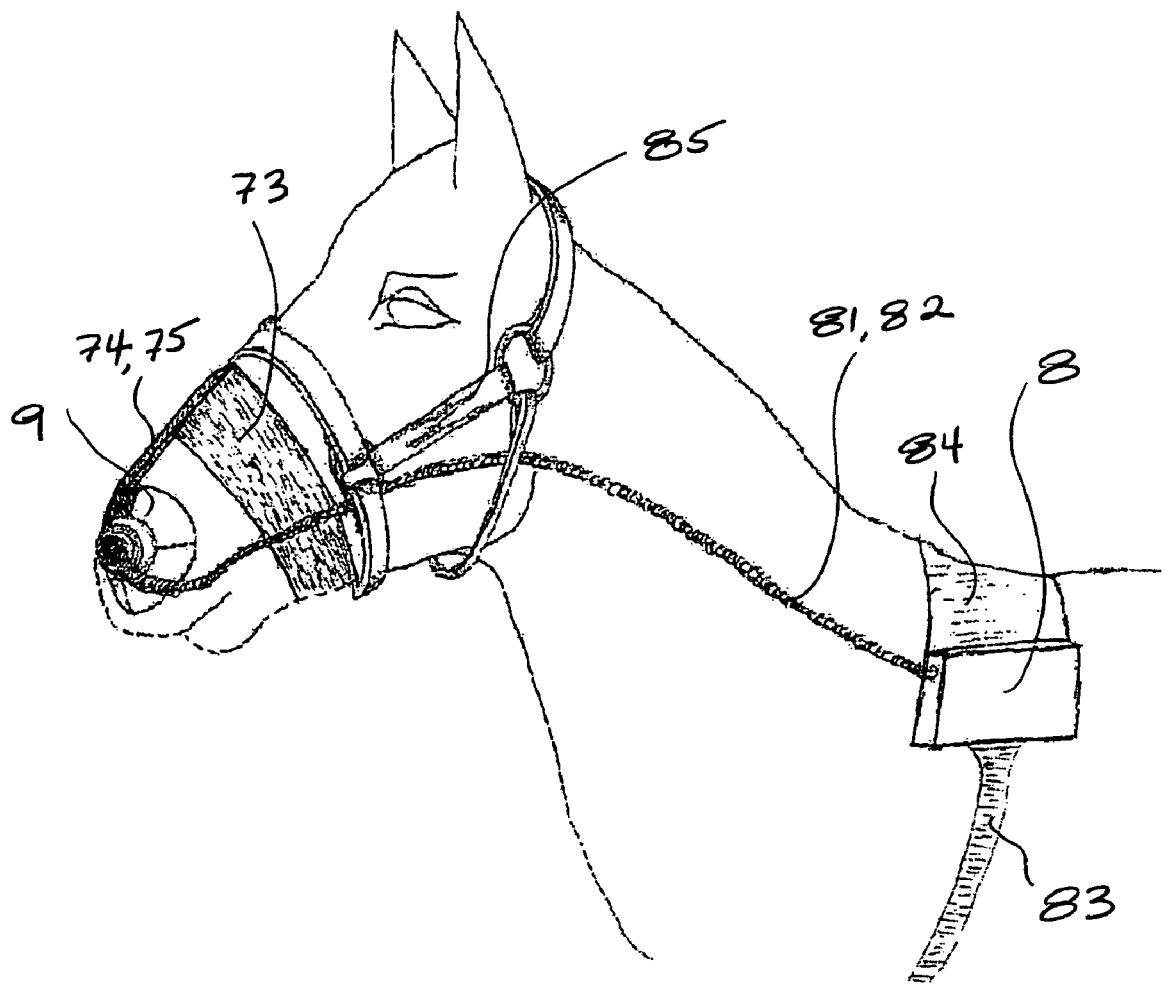
Figure 8:
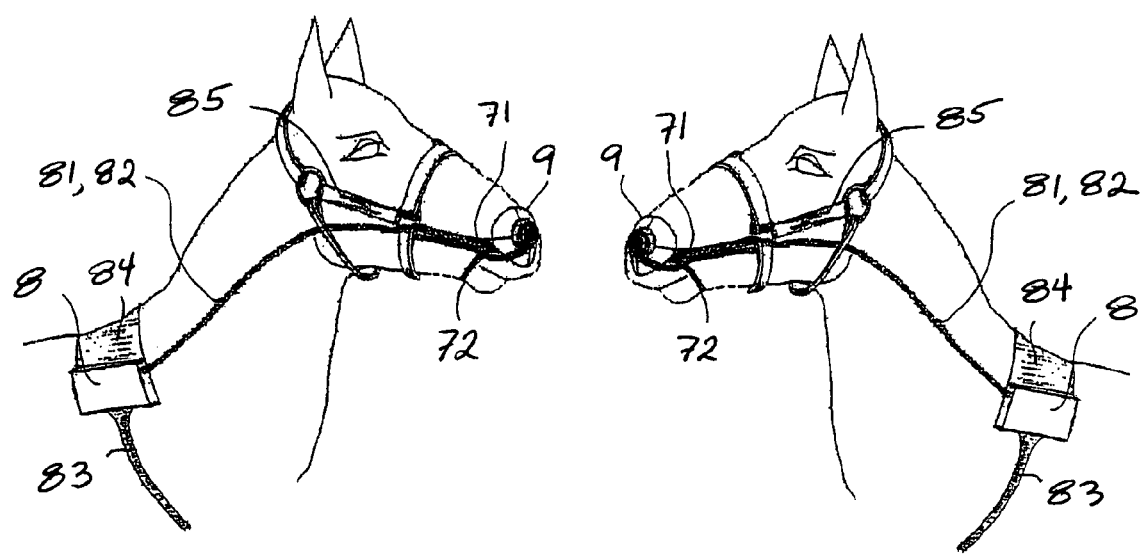

FIG. 1 shows a cross-sectional side view of an inhalation therapy mask for animals according to a first embodiment with an adaptation chamber and an aerosol chamber, whereby a jet nebuliser is provided in the aerosol chamber, FIG. 2 shows a cross-sectional side view of an inhalation therapy mask for animals according to a further embodiment, whereby a diaphragm nebuliser is provided in the aerosol chamber, FIG. 3 shows a cross-sectional side view of an inhalation therapy mask for animals according to a further embodiment, whereby the aerosol chamber is designed to accommodate a spray nebuliser, FIG. 4 shows a cross-sectional side view of an inhalation therapy mask for animals according to a further embodiment, whereby a jet nebuliser is arranged in a nebuliser chamber that is connected to the aerosol chamber by a connector provided for this purpose whereby the inhalation valve is arranged around said connector, FIG. 5 shows a generally left side view of a horse and an inhalation therapy mask for animals according to a further embodiment, whereby pockets are provided on both sides of the horse's back, FIG. 6 shows a generally left side view of a horse and an inhalation therapy mask for animals according to a further embodiment, whereby the mask is secured by a stocking, FIG. 7 shows a generally left side view of a horse and an inhalation therapy mask for animals according to a further embodiment, whereby the size of the stocking is reduced, and FIG. 8 shows a generally right side view of a horse and a generally left side view of the horse, the horse wearing the inhalation therapy mask of FIG. 5.

An inhalation therapy mask according to the invention for animals comprises two mask parts, each with an aerosol chamber, an adaptation chamber and an intermediary dividing wall with a through-opening. These components and other details of a mask part of an inhalation therapy mask according to the invention will be described more precisely in the following with reference to FIGS. 1 to 4. The arrangement of the mask parts on the animal's head and the position of the components required for the aerosol generation will then be described with reference to FIGS. 5 to 7.

FIG. 1 is a cross-sectional view of the structure of a mask part 9 of a first embodiment of an inhalation therapy mask according to the invention. As FIG. 1 shows, a mask part 9 comprises an aerosol chamber 1 to receive an aerosol generated by an aerosol generator 4. The aerosol produced by an aerosol generator 4, such as, for example, a jet nebuliser 45, a diaphragm nebuliser 46, an ultrasonic nebuliser or a spray nebuliser 48, enters the aerosol chamber 1. The aerosol chamber 1 serves as an intermediate store for the aerosol in the exhalation phases during which the animal does not inhale the aerosol together with the respiratory air.

With the embodiment shown in FIG. 1, an aerosol generator 4 to produce the aerosol is arranged in the interior of the aerosol chamber 1 and comprises a nebuliser jet. The nebuliser jet is supplied with compressed air so that a liquid stored in the aerosol generator 4 is entrained and atomised and hence nebulised into the aerosol chamber 1.

According to the invention, the aerosol chamber 1 finally comprises an inhalation opening 11 with an inhalation valve 12. During the inhalation phases, respiratory air passes through the inhalation opening 11 into the aerosol chamber 1, whereby a suitable arrangement of the opening ensures that the aerosol is evacuated from the aerosol chamber 1 in the inhalation phases and does not collect and settle in dead spaces.

As FIG. 1 also shows, a mask part 9 of an inhalation therapy mask according to the invention in each case comprises an adaptation chamber 2 for the adaptation of the mask part 9 to the part of the animal's external body surface surrounding a respiratory opening. For this, the adaptation chamber 2 has an opening arranged directly above the animal's respiratory opening on the edge of which there is a circumferential inwardly curved sealing lip 25. This sealing lip 25 is a continuation of the wall of the adaptation chamber 2 and its wall thickness diminishes in the direction of the opening. To achieve a good seal for the mask on the one hand and avoid the sealing lip 25, with its diminishing thickness in the direction of the opening, being damaged on the other, a circumferential bead 26, preferably with a circular cross section, is provided on the edge 27 of the sealing lip 25. The actual sealing lip and the bead 26 lie on the surface of the animal's body in the immediate vicinity of the respiratory opening and seal the adaptation chamber 2 from the surrounding area.

FIG. 1 also shows that the adaptation chamber 2 has an exhalation opening 21 with an exhalation valve 22. The animal's respiratory air passes out of the exhalation opening 21 during the exhalation phases and in this way leaves the adaptation chamber 2.

Finally, FIG. 1 shows that according to the invention a dividing wall 3 with a through-opening 31 is provided between the aerosol chamber 1 and the adaptation chamber 2. The through-opening 31 is always smaller than the maximum cross section of the aerosol chamber 1, so that according to the invention the aerosol chamber 1 is not fully open to the adaptation chamber 2. In the example of an embodiment shown in FIG. 1, the dividing wall 3 is formed by a part of the wall of the adaptation chamber 2. To ensure that aerosol from the aerosol chamber 1 can enter the adaptation chamber 2 during the inhalation phases, as mentioned above, the through-opening 31 is provided in the dividing wall 3. During the inhalation phases, respiratory air flows through the inhalation opening 11 into the aerosol chamber 1 and from there, together with the aerosol received by the aerosol chamber, passes through the through-opening 31 into the adaptation chamber 2. From there, the animal inhales the respiratory air together with the aerosol.

During the exhalation phase, the respiratory air flows out of the adaptation chamber 2 through the exhalation opening 21. Since the inhalation valve 12 closes the inhalation opening 11 in the aerosol chamber, a pressure is rapidly established in the aerosol chamber 1 that is sufficient in conjunction with the through-opening 31 to prevent large quantities of exhaled air from entering the aerosol chamber 1, interfering with the aerosol received by the aerosol chamber 1 and introducing a significant amount of contaminants into the aerosol chamber 1. The aerosol chamber 1 and its separation from the adaptation chamber 2 by the dividing wall 3 may, in the case of continuous aerosol generation, cause a quantity of aerosol to accumulate in the aerosol chamber 1 during the exhalation phases and this is inhaled by the animal in the subsequent inhalation phase as an aerosol bolus (briefly increased quantity of aerosol).

The dividing wall 3 according to the invention between the two separated chambers 1 and 2 enables the two chambers 1 and 2 each to be optimised for the function assigned to them. For example, the aerosol chamber 1 may be optimised to receive the aerosol generated by an aerosol generator 4, for example by matching its position, size and shape to match the aerosol generator 4.

In the example of an embodiment shown in FIG. 1, this means that the aerosol chamber 1 is designed to accomodate the jet nebuliser 4, 45.

In addition, the division of the two chambers 1 and 2 according to the invention enables the inhalation opening 11 in the aerosol chamber 1 to be selected so that optimum evacuation of the aerosol chamber 1 is achieved when respiratory air flows through the inhalation opening 11 into the aerosol chamber 1 and from there through the through-opening 31 into the adaptation chamber 2 during the inhalation phases.

Supplementary to this, due to the separation of the two chambers 1, 2 according to the invention, the adaptation chamber 2 may be optimally designed to adapt the mask to the animal's physiognomy. This means in particular that the shape of the sealing lip 25 and the opening 28 are optimised to match the surface of the animal's body in the area of the respiratory opening for which the mask part is intended. The design of the sealing lip 25 surrounding the opening 28 in the mask part 9 and placed on the surface of the animal's body may be optimised with regard to the seal. In addition, it is also possible to specify the location of the exhalation opening and the exhalation valve 22 in the adaptation chamber 2 virtually independently of the aerosol generation.

This independence is achieved by the dividing wall 3 according to the invention between the two chambers 1 and 2, which are, however, connected by the through-opening 31 in the dividing wall 3. The dividing wall 3 prevents a direct flow of a significant quantity of respiratory air entering the aerosol chamber 1 and interfering with the aerosol generation or storage.

The possibility of adapting the aerosol chamber 2 to the surface of the animal's body in the immediate vicinity of the respiratory opening, minimises the area of the body surface exposed to the aerosol, so that virtually no aerosol is able to settle on the body surface.

The function of the dividing wall 3 according to the invention can be further supported by the provision of a separating valve 32 on the through-opening 31, the said valve being closed in the exhalation phases and open in the inhalation phases. This valve ensures that the through-opening 31 is reliably closed in the exhalation phases so that the respiratory air cannot enter the aerosol chamber 1 in the exhalation phases.

As FIG. 1 shows, the aerosol chamber 1 is connected detachably to the adaptation chamber 2 so that both chambers 1 and 2 can be easily cleaned. To ensure that the two chambers 1 and 2 can be separated from each other, the aerosol chamber 1 has a first latching device 35 on the side facing the adaptation chamber 2, preferably in the form of a circumferential latching projection. The adaptation chamber 2 correspondingly has a second latching device 36 that may, for example, take the form of a circumferential latching groove into which the latching projection latches when the aerosol chamber 1 is placed on the adaptation chamber 2. Both the first latching device 35 and the second latching device 36 are advantageously designed so that the aerosol chamber 1 may be rotated in relation to the adaptation chamber 2 thus enabling an optimum position to be chosen for the aerosol chamber 1 after the mask has been attached to the animal's head; this is in particular of advantage when, as shown in FIG. 1, the aerosol generator 4 is integrated in the aerosol chamber 1. If there is no need for separable chambers that can be easily cleaned, the connection between the two chambers can still be advantageously designed so that the aerosol chamber 1 may be positioned (rotated) in relation to the adaptation chamber 2. The positionability is advantageously provided about an axis of rotation A—A.

FIG. 1 also shows with reference to the adaptation chamber 2 that the circumferential sealing lip 25 is preferably designed in such a way that there is a sputum collection area 29 in the lower area that helps to ensure that any possible contamination in the adaptation chamber 2 of the mask part is as far as possible restricted to adaptation chamber 2 and does not enter the aerosol chamber 1 although protection is already provided by the dividing wall 3 according to the invention between the two chambers 1, 2. The design of the sealing lip 25 as a sputum trap helps to protect the aerosol chamber 1 against contamination in particular during the exhalation phases.

FIG. 2 shows a second example of an embodiment in which according to the invention the mask part 9 shown also comprises an aerosol chamber 1 and an adaptation chamber 2 separated from each other by a dividing wall 3 with a through-opening 31. The aerosol chamber 1 has an inhalation opening 11 with an inhalation valve 12. In the example of an embodiment shown in FIG. 2, the aerosol is generated by a diaphragm nebuliser 4, 46 that nebulises a stored liquid and releases it into the aerosol chamber 1. In the example of an embodiment shown in FIG. 2, advantageously the inhalation opening 11 with the inhalation valve 12 is arranged opposite to the aerosol generator 4, 46 so that, during the inhalation phases, the respiratory air entering the aerosol chamber 1 evacuates all the aerosol released into the aerosol chamber 1 from the aerosol chamber 1. During the exhalation phases, in which the respiratory air flows out of the adaptation chamber 2 through the exhalation opening 21, when in continuous operation, the aerosol generator 4, 46 releases a quantity of aerosol into the aerosol chamber 1 which is then stored in the aerosol chamber 1 until the next inhalation phase. The dividing wall 3 adequately protects this quantity of aerosol against contamination by the exhaled air. A further improvement of the protection is achieved by the valve 32 on the through-opening shown in FIG. 1.

Otherwise, the structure of the adaptation chamber 2 corresponds to the structure of the adaptation chamber 2 in the first example of an embodiment and reference is hereby made to the description thereof.

In the third example of an embodiment shown in FIG. 3, the mask part 9 of the inhalation therapy mask according to the invention shown again comprises an aerosol chamber 1 and an adaptation chamber 2 plus a dividing wall 3 with a through-opening 31 separating the two chambers 1 and 2. In the third example of an embodiment, the aerosol generator 4, 48 is a spray nebuliser 48 which releases the aerosol spray into the aerosol chamber 1, where the aerosol generated in this way is stored for a short time. According to the invention, in this example of an embodiment, the aerosol chamber 1 again comprises an inhalation opening 11 with an inhalation valve 12 that in the specific design in the third example of an embodiment is arranged on the opening 51 through which the aerosol is introduced into the aerosol chamber 1 by means of the spray nebuliser 48.

For usage in accordance with the third example of an embodiment, ie in conjunction with a spray nebuliser 48, reference is made to the fact that it is often sufficient to place only one mask part 9 on one of the animal's respiratory openings when a sufficient quantity of spray has been released into the aerosol chamber 1. In the next inhalation phase, the animal then inhales the spray nebuliser stored in the aerosol chamber 1, whereupon the mask part 9 may be removed again from the animal's respiratory opening. If required, more spray is released into the aerosol chamber 1 and the mask part 9 placed on the animal's respiratory opening so that the aerosol spray is inhaled in the next inhalation phase. Advantageously, therefore, the inhalation therapy mask according to the invention is designed so that the two mask parts 9 can be separated from each other so that only one mask part 9 has to be handled for the advantageous application in conjunction with a spray nebuliser.

With the example of an embodiment shown in FIG. 4, the mask part 9 of the inhalation therapy mask according to the invention again comprises an aerosol chamber 1 and an adaptation chamber 2 and a dividing wall 3 with a through-opening 31 separating the two chambers. FIG. 4 also shows a separating valve 32 that is open in the inhalation phases and closed in the exhalation phases. In the example of an embodiment shown in FIG. 4, the inhalation valve 12 on the inhalation opening 11 in the aerosol chamber 1 is arranged around a connector 53 for a nebuliser 65. The connector is designed to enable the connection of the aerosol outlet from a nebuliser 65. The example of an embodiment shown in FIG. 4 is a jet nebuliser in which the nebuliser jet is arranged in a nebuliser chamber. The aerosol generated in the nebuliser chamber 6 is fed through the aerosol outlets 55 and in this way enters the aerosol chamber 1. In the example of an embodiment shown, there is an incoming air pipe 66 in the nebuliser chamber 6 that terminates above the jet nebuliser 65 and through which respiratory air flows during the inhalation phases, which guarantees that the aerosol is transported out of the nebuliser chamber 6 into the aerosol chamber 1. In the exhalation phases, the compressed air supplied for the aerosol generation ensures that the aerosol is transported in the aerosol chamber 1.

FIGS. 5 and 8 are an overview of the arrangement of an inhalation therapy mask according to the invention for animals using the example of a horse. One mask part 9 placed on the left-side respiratory opening is shown in FIGS. 5 and 8. The second mask part 9 is arranged correspondingly on the other side, the right-side, which is shown in FIG. 8. The two mask parts are connected to each other so they may be handled jointly and are each secured by a strap 71 to a halter conventionally present on the horse's head. A chin strap 72 may be provided for further fixation.

In the embodiment shown in FIGS. 5 and 8, pockets 8 are provided on both sides of the horse's back, each of which is assigned to one of the mask parts 9, containing supply components for the aerosol generator or the actual aerosol generator.

The supply components for compressed air aerosol generators are compressors and the power supply required for this. In this case, compressed air is fed through a hose pipe 81 to the aerosol generator 4 on/in the mask, which—as described, for example, with regard to FIG. 1—is assigned to one mask part 9 in the aerosol chamber 1. If the actual aerosol generator 4 is arranged in the pocket, a suitable hose pipe 81 supplies the aerosol to the aerosol chamber 1. In the case of a diaphragm nebuliser 46, the pocket 8 preferably contains the power supply and the control element so that electric lines 82 may be run to the mask parts 9.

The two pockets are secured to the animal by means of a strap 83, 84.

Arranging the supply components or the aerosol generators on the animal's back has the advantage that these components do not have to be positioned in front of the animal, for example on a table or on the floor of the stall. The animal is able to move with the nebuliser components on its back without any risk of the aerosol generation being impaired or interrupted. As FIG. 5 shows, the lines 81, 82 are correspondingly secured to the halter 85 or in some other way to the animal's body.

If no halter is available, the two mask parts 9 in the inhalation therapy mask according to the invention may be integrated in a type of stocking 73 that is pulled over the animal's head, as shown in FIG. 6. The two mask parts 9 are connected to each other by the stocking 73 and form a two-part inhalation therapy mask according to the invention. The mask parts 9 are secured by the suitably dimensioned and elastic stocking 73.

FIG. 7 shows another design of a holder on the animal's head in which the size of the stocking 73 has been reduced so that the two mask parts are no longer arranged in the stocking. There is a holding plate 74 or holding rod 75 on the stocking to which the two mask parts 9 are secured. The mask parts 9 are preferably fastened to the holding plate 74/holding rod 75 in such a way that they may be positioned in relation to the animal's respiratory openings. The design, dimensional stability and elasticity of the holding plate 74/holding rod 75 ensure the secure positioning of the mask parts 9 on the animal's respiratory openings.

The invention claimed is:

1. Inhalation therapy mask for an animal, the mask comprising:
    two mask parts with each mask part being designed to be arranged over one of the animal's respiratory openings and each mask part comprising:
    a. an aerosol chamber for receiving an aerosol generated by an aerosol generator comprising an inhalation opening with an inhalation valve through which the respiratory air enters the aerosol chamber during the inhalation phases
    b. an adaptation chamber
        i. which is designed for the adaptation of the mask part to the external surface of the animal's body surrounding a respiratory opening,
        ii. with an opening directed toward the animal's respiratory opening provided with a circumferential inwardly curved sealing lip on its edge, and
        iii. with an exhalation opening with an exhalation valve through which respiratory air from the adaptation chamber escapes during the exhalation phases, and c. a dividing wall between the aerosol chamber and the adaptation chamber with a through-opening through which an aerosol present in the aerosol chamber enters the adaptation chamber together with the respiratory air from the aerosol chamber during the inhalation phases.

2. Inhalation therapy mask for an animal according to claim 1, further comprising a separating valve in the through-opening that is designed to be open during the inhalation phases and closed during the exhalation phases.

3. Inhalation therapy mask for an animal according to claim 1, wherein the aerosol chamber is held in a positionable way on the adaptation chamber to enable the chambers to be aligned in relation to each other.

4. Inhalation therapy mask for an animal according to claim 3 further comprising a first latching device and a second latching device, wherein the first latching device is provided on the aerosol chamber and interacts with the second latching device provided on the adaptation chamber to hold the aerosol chamber on the adaptation chamber.

5. Inhalation therapy mask for an animal according to claim 4, wherein the first latching device is designed as a latching projection and the second latching device is designed as a latching groove.

6. Inhalation therapy mask for an animal according to claim 5, wherein the latching projection is located on the circumference of one of the aerosol chamber and the adaptation chamber and the latching groove is located on the circumference of the other of the aerosol chamber and the adaptation chamber so that the chambers may be rotated in relation to each other.

7. Inhalation therapy mask for an animal according to claim 1, wherein the aerosol chamber may be separated from the adaptation chamber.

8. Inhalation therapy mask for an animal according to claim 1, wherein the sealing lip is a continuation of a wall of the adaptation chamber.

9. Inhalation therapy mask for an animal according to claim 8, wherein the sealing lip has a thickness that diminishes in the direction of the adaptation chamber opening.

10. Inhalation therapy mask for an animal according to claim 8 wherein the sealing lip has a bead on edge facing the adaptation chamber opening.

11. Inhalation therapy mask for an animal according to claim 10 wherein the bead is made of solid material.

12. Inhalation therapy mask for an animal according to claim 1, wherein the two mask parts are separable from one another to allow the handling of an individual mask part.

13. Inhalation therapy mask for an animal according to claim 1, wherein the two mask parts are connected to a holding device for fixing the mask parts to the animal's head in relation to the respiratory opening.

14. Inhalation therapy mask for an animal according to claim 13, wherein the holding device comprises holding straps.

15. Inhalation therapy mask for an animal according to claim 13, wherein the holding device comprises a holding band or holding stocking.

16. Inhalation therapy mask for an animal according to claim 13, wherein the holding device comprises an elastic holding plate or an elastic holding rod to which the mask parts are secured.

* * * * *